US00PP09747P

United States Patent [19]

Dümmen

[11] Patent Number: Plant 9,747

[45] Date of Patent: Dec. 10, 1996

[54] GERANIUM PLANT NAMED 'HWD VENTURA'

[75] Inventor: Günter Dümmen, Rheinberg-Eversael, Germany

[73] Assignee: Dummen Jungpflanzenkulturen, Rheinberg-Eversael, Germany

[21] Appl. No.: 521,402

[22] Filed: Aug. 30, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Proprietary Rights International

[57] ABSTRACT

A new and distinct cultivar of geranium plant named HWD Ventura, characterized by its semi-double bright red flowers; medium to large umbels; compact plant size; and freely branching plant habit.

1 Drawing Sheet

The present invention relates to a new and distinct cultivar of geranium plant, botanically known as *Pelargonium×hortorum,* known as the variety Duevent, and hereinafter referred to by the cultivar name HWD Ventura.

The new cultivar is a product of a planned breeding program conducted by the inventor in Rheinberg, Germany. The objective of the breding program was to develop a new freely branching, semi-double geranium with bright red-colored flowers.

The new cultivar originated from a cross made by the inventor of the nonpatented cultivar Robe as the male or pollen parent with the nonpatented cultivar Perlenkette Orange as the female or seed parent.

The cultivar HWD Ventura was discovered and selected by the inventor as a flowering plant within the progeny of the stated cross in a controlled environment in Rheinberg, Germany. Asexual reproduction of the new cultivar by terminal cuttings taken at Rheinberg, Germany, has shown that the unique features of this new geranium are stabilized and reproduced true to type in successive generations of asexual reproduction.

The following traits have been repeatedly observed and are determined to be the unique characteristics of HWD Ventura. These characteristics in combination distinguish HWD Ventura as a new and distinct cultivar:

1. Semi-double bright red flowers.
2. Medium to large umbels.
3. Compact plant size.
4. Freely branching.

In comparison to the parent cultivar Robe, plants of the new geranium have larger umbels, lighter petal color, and zonation pattern on the foliage. In comparison to the parent cultivar Perlenkette Orange, plants of the new geranium have larger umbels, darker petal color, zonation pattern on the foliage, and more compact plant habit.

The new geranium is similar in petal color to the patented cultivar Kleflam (U.S. Plant Pat. No. 8,551). Compared to plants of the cultivar Kleflam, plants of the new geranium have larger umbels, fewer flowers per umbel, shorter peduncles, and lighter green foliage color.

The accompanying colored photograph illustrates the overall appearance of the new cultivar, showing the colors as true as it is reasonably possible to obtain in colored reproductions of this type. Flower color appears more red than the actual flower color due to light reflectance. The photograph comprises a top perspective view of a typical potted plant of HWD Ventura with one plant in a 10-cm container.

The cultivar HWD Ventura has not been observed under all possible environmental conditions. The phenotype may vary somewhat with variations in environment such as temperature and light intensity, without, however, any variance in genotype. The following observations, measurements and comparisons describe plants grown in Rheinberg, Germany, under commercial practice in a glass-covered greenhouse with day temperatures of 24° C. and night temperatures of 18° to 20° C. and light levels of 45,000 to 60,000 lux. Plants were grown in 10-cm pots with one plant per pot.

In the following description, color references are made to The Royal Horticultural Society Colour Chart except where general terms of ordinary dictionary significance are used.

Classification:

*Botanical.*—*Pelargonium×hortorum.*

*Commercial.*—Zonal geranium.

*Cultivar.*—'HWD Ventura'.

Parentage:

*Male parent.*—Cultivar Robe.

*Female parent.*—Cultivar Perlenkette Orange.

Propagation:

*Type cutting.*—Terminal cuttings.

*Time to initiate roots.*—Summer: 27° C., 21 days; winter: 20° C., 28 days.

Plant Description

General appearance: Rounded; compact plant size; upright; freely branching.

Foliage description:

*Arrangement.*—Generally alternate.

*Shape.*—Orbicular with rounded tip and cordate base.

*Size.*—Length: 7 to 8 cm. Width: 7.5 to 8.5 cm.

*Texture.*—Velvety; pubescent on upper and under surfaces.

*Margin.*—Crenate.

*Color.*—Young foliage, upper surface: 137C. Young foliage, under surface: 147B. Mature foliage, upper surface: 137C. Mature foliage, under surface: 147B. Zone, upper surface: 147A. Zone, under surface: None. Veins, upper surface: 145A. Veins, under surface: 145B. Petiole: 144A.

*Zonation.*—Width of zone: 1.5 to 2 cm. Location of zone: 1 cm from margin and 2.5 cm from petiole.

*Venation pattern.*—Palmate.

*Petiole.*—Length : 7.5 cm. Diameter: 2 to 2.5 mm.

Stem description:

*Internode length.*—1.3 cm.

*Stem color.*—144A.

*Lateral branch number.*—9.

*Lateral branch length.*—5 to 10 cm.

Flowering Description

Flowering habit: Freely flowering. Flowers arranged in umbels.

Natural flowering season: Year-round.

Flowers borne: Flower buds develop in apical leaf axils. Umbels are displayed above the foliage.

Quantity of inflorescences: Very floriferous; usually 6 open umbels and at least 6 developing umbels per plant at one time.

Umbels:

*Form.*—Rounded.

*Diameter.*—9.5 cm.

*Depth (height).*—7 cm.

Flowers:

*Form.*—Semi-double.

*Shape.*—Rounded.

*Quantity of flowers per umbel.*—20.

*Diameter.*—4.5 to 5 cm.

*Depth (height).*—2 cm.

Petals:

*Shape.*—Obovate with rounded tip.

*Arrangement.*—Rosette, overlapping.

*Quantity.*—6.

*Aspect.*—Flat.

*Size.*—Length: 2.2 to 2.5 cm. Width: 2.3 to 2.5 cm.

*Texture.*—Satiny, smooth.

*Margin.*—Entire.

*Color.*—When opening, upper surface: 46C. When opening, under surface: 46D. Upper surface: 46C. Under surface: 46D, venous areas, 46A. Fading to, upper surface: 43A. Fading to, under surface: 36D near sepals.

Petaloids:

*Shape.*—Irregular, generally obovate with rounded or clefted tip.

*Arrangement.*—Rosette, overlapping.

*Quantity.*—4 to 5.

*Size.*—Length: 2 cm. Width: 1 to 1.5 cm.

*Texture.*—Satiny, smooth.

*Margin.*—Generally entire.

*Color.*—When opening, upper surface: 46C. When opening, under surface: 46D. Upper surface: 46C. Under surface: 46D, venous areas 46A. Fading to, upper surface: 43A. Fading to, under surface: 36D, near sepals.

Peduncle (umbel stem):

*Angle.*—Erect.

*Length.*—14 to 15 cm.

*Pubescence.*—Very fine.

*Color.*—144A.

Pedicel (individual flower stem):

*Angle.*—Erect, rigid.

*Length.*—3 cm.

*Pubescence.*—Very fine.

*Color.*—144A.

Flower bud:

*Shape.*—Ovoid.

*Length.*—1.4 cm.

*Diameter.*—8 mm.

*Color.*—44A.

Sepals:

*Arrangement.*—Rosette.

*Quantity.*—5.

*Size.*—Length: 8 to 9 mm. Width: 2 to 3 mm.

*Shape.*—Acuminate with apiculate tip.

*Texture.*—Velvety.

*Margin.*—Entire.

*Color.*—Upper surface: 46A at base fading to 144A at tip. Under surface: 46A at base fading to 144A at tip.

Reproductive organs:

*Androecium.*—Stamen number: 10 to 12. Anther size: 2 mm. Anther color: 43A. Pollen color: 34C.

*Gynoecium.*—Pistil number: 1. Pistil length: 9 mm. Stigma shape: Decurrent. Stigma color: 63A. Style length: 4 mm. Style color: 63A.

Ploidy level: Tetraploid.

Disease resistance: No fungal, bacterial nor viral problems observed.

Seed development: Seed production is very rarely observed.

It is claimed:

1. A new and distinct cultivar of geranium plant named HWD Ventura, as illustrated and described.

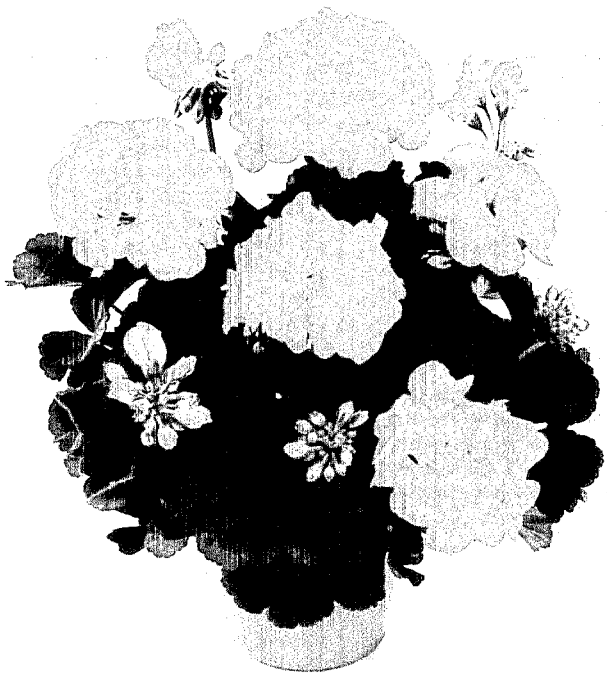

* * * * *